US010866223B2

(12) United States Patent
Balasubramanian et al.

(10) Patent No.: US 10,866,223 B2
(45) Date of Patent: Dec. 15, 2020

(54) COLORIMETRIC DETECTION AND QUANTITATIVE ESTIMATION OF PERACIDS USING A REDOX SENSITIVE LEUCO DYE

(71) Applicant: ECOLAB USA INC., Saint Paul, MN (US)

(72) Inventors: Ramakrishnan Balasubramanian, Saint Paul, MN (US); Junzhong Li, Saint Paul, MN (US)

(73) Assignee: Ecolab USA Inc., Saint Paul, MN (US)

( * ) Notice: Subject to any disclaimer, the term of this patent is extended or adjusted under 35 U.S.C. 154(b) by 314 days.

(21) Appl. No.: 15/843,168

(22) Filed: Dec. 15, 2017

(65) Prior Publication Data
US 2018/0172651 A1    Jun. 21, 2018

Related U.S. Application Data

(60) Provisional application No. 62/434,554, filed on Dec. 15, 2016.

(51) Int. Cl.
*G01N 31/00* (2006.01)
*G01N 31/22* (2006.01)
(Continued)

(52) U.S. Cl.
CPC ........... *G01N 31/228* (2013.01); *G01N 21/78* (2013.01); *G01N 33/18* (2013.01)

(58) Field of Classification Search
CPC .................................................. G01N 31/228
(Continued)

(56) References Cited

U.S. PATENT DOCUMENTS 2,833,813 A   5/1958  Wallace
4,385,114 A   5/1983  Güthlein et al.
(Continued)

FOREIGN PATENT DOCUMENTS

DE   19651797 A1   6/1998
EP    0322631 A1   7/1989
(Continued)

OTHER PUBLICATIONS

Zhao et al. "Molecular-Level Insights into Intrinsic Peroxidase-Like Activity of Nanocarbon Oxides" Chem. Eur. J. 2015, 21, 960-964, plus supporting information (Year: 2015).*

(Continued)

*Primary Examiner* — Christine T Mui
*Assistant Examiner* — Emily R. Berkeley
(74) *Attorney, Agent, or Firm* — McKee, Voorhees & Sease, PLC

(57) ABSTRACT

A composition, method and kit for quantifying the concentration of one peracid or the total concentration of two or more peracids in a water source are disclosed. In particular, an oxidation sensitive or peroxycarboxylic acid selective leuco dye is used to react only with one or more peroxycarboxylic acids in a water source but not with peroxide usually co-existing in the water source. Not only does the oxidation sensitive or peroxycarboxylic acid selective leuco dye react with peracid(s) but also the reaction generates a color species that can be used visually or through absorbance measurement to quantify the peracid concentration. The method disclosed here is not a titration method, it involves a simple mixing step. The kit or composition disclosed here does not utilize a catalyst, such as iodine.

19 Claims, 5 Drawing Sheets
(2 of 5 Drawing Sheet(s) Filed in Color)

(51) Int. Cl.
*G01N 21/78* (2006.01)
*G01N 33/18* (2006.01)

(58) Field of Classification Search
USPC .......................................................... 436/129
See application file for complete search history.

(56) References Cited

U.S. PATENT DOCUMENTS

| | | | |
|---|---|---|---|
| 4,794,079 | A | 12/1988 | Buckler et al. |
| 4,900,682 | A | 2/1990 | Fischer et al. |
| 4,908,323 | A | 3/1990 | Werner |
| 5,081,044 | A | 1/1992 | Buckler et al. |
| 5,314,687 | A | 5/1994 | Oakes et al. |
| 7,156,178 | B2 | 1/2007 | Rae et al. |
| 7,829,020 | B2 | 11/2010 | Pagoria et al. |
| 8,226,939 | B2 | 7/2012 | Herdt et al. |
| 8,344,026 | B2 | 1/2013 | Li et al. |
| 8,425,775 | B2 | 4/2013 | Post et al. |
| 8,809,392 | B2 | 8/2014 | Li et al. |
| 8,846,107 | B2 | 9/2014 | Li et al. |
| 8,871,807 | B2 | 10/2014 | Gohl et al. |
| 8,877,254 | B2 | 11/2014 | Li et al. |
| 8,933,263 | B2 | 1/2015 | Herdt et al. |
| 9,018,142 | B2 | 4/2015 | Rovison, Jr. et al. |
| 9,244,016 | B2 | 1/2016 | Karato et al. |
| 9,253,978 | B2 | 2/2016 | Li et al. |
| 9,359,295 | B2 | 6/2016 | Li et al. |
| 9,365,509 | B2 | 6/2016 | Kraus et al. |
| 2004/0033269 | A1* | 2/2004 | Hei .................. A01N 25/02 424/616 |
| 2016/0176814 | A1 | 6/2016 | Balasubramanian et al. |
| 2016/0176815 | A1 | 6/2016 | Li et al. |
| 2017/0071200 | A1 | 3/2017 | McSherry et al. |

FOREIGN PATENT DOCUMENTS

| | | |
|---|---|---|
| WO | 9002339 A1 | 3/1990 |
| WO | 9222806 A1 | 12/1992 |
| WO | 2004005246 A2 | 1/2004 |
| WO | 2007044666 A2 | 4/2007 |
| WO | 2016025714 A1 | 2/2016 |
| WO | 2017044806 A1 | 3/2017 |

OTHER PUBLICATIONS

Joshephy et al. "The Horseradish Peroxidase-catalyzed Oxidationof 3,5,3',5'-Tetramethylbenzidine" The Journal of Biological Chemistry. vol. 257, No. 7, Issue of Apr. 10, pp. 3669-3675, 1982 (Year: 1982).*

ECOLAB USA Inc., PCT/US2017/066585 filed Dec. 15, 2017, "The International Search Report and the Written Opinion of the International Searching Authority, or the Declaration", dated Apr. 3, 2018.

Minning, Stefan et al., "Determination of Peracid and Putative Enzymatic Peracid Formation by an Easy Colorimetric Assay", Analytica Chimica Acta 378 (1999) pp. 293-298.

Pinkernell, Ulrich et al., "Selective Photometric Determination of Peroxycarboxylic Acids in the Presence of Hydrogen Peroxide", Journal Homepage, The Analyst, Jun. 1997, vol. 122 (pp. 567-571).

* cited by examiner

COLORIMETRIC DETECTION AND QUANTITATIVE ESTIMATION OF PERACIDS USING A REDOX SENSITIVE LEUCO DYE

CROSS-REFERENCE TO RELATED APPLICATIONS

This application claims priority under 35 U.S.C. § 119 to provisional application U.S. Ser. No. 62/434,554 filed Dec. 15, 2016, herein incorporated by reference in its entirety. The entire contents of this patent application are hereby expressly incorporated herein by reference including, without limitation, the specification, claims, and abstract, as well as any figures, tables, or drawings thereof.

FIELD OF THE INVENTION

The disclosure relates to use of a redox sensitive leuco dye for quantifying a peracid concentration in a water source or a peracid composition. Various water sources and/or a peracid compositions can employ a redox sensitive leuco dye for quantifying their peracid concentrations, including for example those used in oil and gas operation, during which the peracid concentration needs to be measured or monitored constantly. The present disclosure enables almost anyone to quantify a peracid or mixture of peracids in real time and on-site, without the need to collect a sample, send the sample to a remote laboratory or do a titration, and wait for the result before assessing the concentration for adjustments thereto.

BACKGROUND OF THE INVENTION

Peracids (also referred to synonymously herein as peroxycarboxylic acids), as well as mixed peracid systems, are known for use as antimicrobials and bleaching agents in a variety of industries. Hereinafter, peracids and peroxycarboxylic acids are used interchangeably in this disclosure. Peracetic acid or peroxyacetic acid (PAA or POAA) (dynamic equilibrium mixture of POAA/PAA, $H_2O_2$, $H_2O$ and AA) have been used in the food and beverage industries as a fast acting, "green" antimicrobial. Such products demonstrate beneficial properties towards oxidizing solids and improving water quality. In addition, compared to other commercially available biocides, the use of peroxyacetic acid results in a low environmental footprint due in part to its decomposition into innocuous components (e.g. acetic acid (AA), oxygen, $CO_2$ and $H_2O$). See for example, U.S. Pat. No. 8,226,939, entitled "Antimicrobial Peracid Compositions with Selected Catalase Enzymes and Methods of Use in Aseptic Packaging," which is incorporated by reference in its entirety.

Peroxycarboxylic acids have also been used for certain water treatment applications in the area of commercial oil and gas operations because there remains a need for enhanced water treatment methods. See for example U.S. Pat. No. 9,018,142, entitled "Peracetic Acid Oil-Field Biocide and Method," and U.S. Pat. No. 7,156,178, which are incorporated by reference in their entirety. For example, from a microbiology perspective, mitigation of microorganisms is essential to minimize environmental concerns for waste products and to avoid contamination of systems such as well or reservoir souring and/or microbiologically-influenced corrosion (MIC). As a result, prior to the drilling and fracking steps, water is treated to restrict the introduction of microbes into the well or reservoir. This also acts to prevent microbes from having a negative effect on the integrity of the fluids. In addition, before disposal, flow-back water is treated to abide environmental restrictions stipulated by regulatory agencies.

For the purpose of mitigation of microorganisms, it is essential to have an effective level of the peroxycarboxylic acid(s) in a treated water source. In oil and gas operations, an accurate estimation for the volume of a particular water source needed to be treated is usually difficult because the container for the water source is usually anything but a regular container. The difficulty to have an accurate water volume requires the actual level of peroxycarboxylic acid to be monitored during peroxycarboxylic acid dosing or application. In addition, peroxycarboxylic acids and hydrogen peroxide are prone to quenching from common, naturally occurring chemicals which can severely limit their utility. Over dosing may be effective for controlling microorganisms but is not desirable.

Despite its fast action and eco-friendly properties, the use of peroxycarboxylic acids, including peroxyacetic acid, has a number of drawbacks for use in water treatment methods for oil and gas production. For example, high dosages of the peroxycarboxylic acids can increase the corrosion rates in pipelines and equipment due in part to the presence of hydrogen peroxide ($H_2O_2$). Moreover, the peroxycarboxylic acids/$H_2O_2$ can interfere with the activity of functional agents necessary for the methods of water treatment in oil and gas recovery, including friction reducers and thickeners which are often critical for the fracking process. Because of these drawbacks, use of peroxycarboxylic acids in oil and gas production for water treatment needs constant monitoring in order to prevent the existence of a high concentration peroxycarboxylic acid in a water source and potential damage thereof or an ineffective concentration.

Quantification of peroxycarboxylic acids has often relied on titration techniques or colorimetric dye that are cumbersome or complicated to use. There is a need for a simpler analytical procedure that can determine the concentration of a peroxycarboxylic acid in oil and gas operations. In light of the foregoing, there remains a demand for improved methods, compositions, and kits for quantifying a peroxycarboxylic acid concentration in real time and on site.

Accordingly, it is an objective of the disclosure to provide a composition, method and kit for quantifying a peroxycarboxylic acid in a water source or in a peroxycarboxylic acid composition.

Other objects, advantages and features of the present disclosure will become apparent from the following specification taken in conjunction with the accompanying drawings.

BRIEF SUMMARY OF THE INVENTION

The present disclosure provides a method of using a redox sensitive leuco dye to quantify the peroxycarboxylic acid concentration in a water source, especially a water source used in oil and gas operations. Traditional methods for determining a concentration of a peroxycarboxylic acid in a solution usually involve a titration method which requires a certain laboratory setup, standard solution preparation, instrument calibration, and a multiple step procedure. These traditional methods are difficult to use in a typical oil and gas operation, where the concentration of a peroxycarboxylic acid composition or water source needs to be determined on site and in real time before the water source is used in the operation or released into the environment.

In one aspect, the present disclosure provides a peroxycarboxylic acid quantification composition comprising a redox sensitive leuco dye and a peroxycarboxylic acid composition; wherein the peroxycarboxylic acid composition comprises a $C_1$-$C_{22}$ peroxycarboxylic acid, the redox sensitive leuco dye selectively reacts with the peroxycarboxylic acid in the peroxycarboxylic acid composition to form a colored species, the leuco dye does not react with hydrogen peroxide, and the colored species exhibits a stable absorbance within about 20 minutes at a visible light wavelength and the absorbance intensity linearly proportional to the concentration of the peroxycarboxylic acid of between about 1 ppm and about 100 ppm, or more precise ranges there between.

In another aspect, the present disclosure provides a method of quantifying a peroxycarboxylic acid concentration in a treated water source. The method comprises providing a water source (a sample of a water source), contacting the water source with a redox sensitive leuco dye to form a peroxycarboxylic acid quantification composition, and measuring an absorbance of the peroxycarboxylic acid quantification composition at a visible light wavelength to quantify the peroxycarboxylic acid by using the absorbance-peroxycarboxylic acid concentration standard curve or by comparing the color of the peroxycarboxylic acid quantification composition against a color-peroxycarboxylic acid concentration chart; wherein the water source comprises a $C_1$-$C_{22}$ peroxycarboxylic acid, a $C_1$-$C_{22}$ carboxylic acid, hydrogen peroxide, or a combination thereof.

In yet another aspect, the present disclosure provides a colorimetric assay kit. The kit comprises a clear and colorless vial containing a redox sensitive leuco dye, and a color—peroxycarboxylic acid concentration chart, wherein the vial can receive a certain amount of a peroxycarboxylic acid composition or a water source, and optionally instructions for use.

While multiple embodiments are disclosed, still other embodiments of the present disclosure will become apparent to those skilled in the art from the following detailed description which shows and describes illustrative embodiments of the disclosure. Accordingly, the drawings and detailed description are to be regarded as illustrative in nature and not restrictive.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Figure 1:
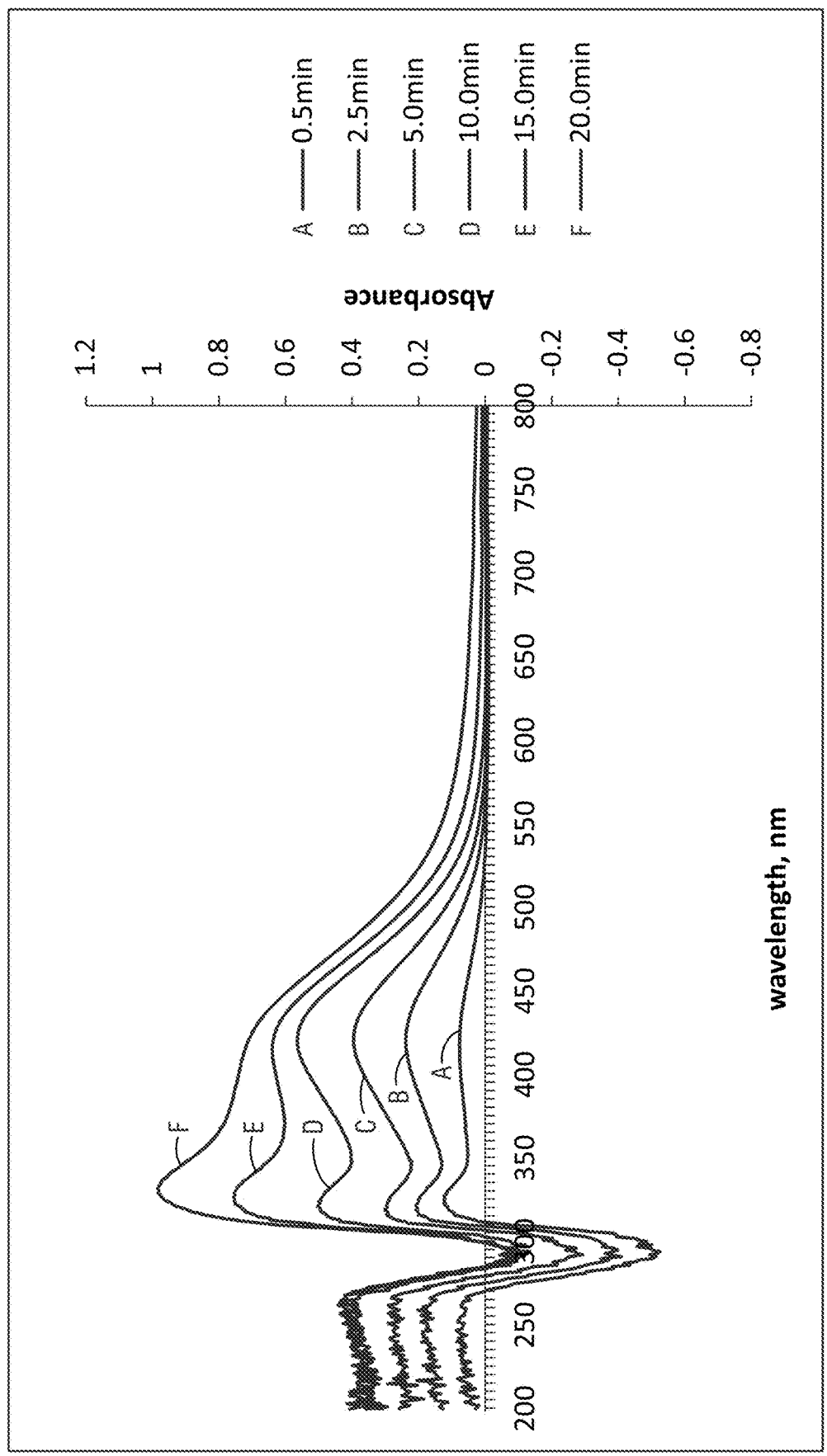
FIG. 1 shows the absorbance spectra of the mixture of a peracetic acid composition and 3,3',5,5'-tetramethylbenzidine (TMB) at different times after the mixture formation.

The present disclosure relates to compositions, methods, and kits that comprise a redox sensitive leuco dye for quantifying a peroxycarboxylic acid concentration in a sample. The sample can be an antimicrobial peroxycarboxylic acid composition that is in turn used to treat a water source. The sample can be an antimicrobial peroxycarboxylic acid composition used to treat various hard surfaces, such as health care surfaces, instruments, and medical instruments in need of sanitation. The sample can also be a water source that has been treated previously by an antimicrobial peroxycarboxylic acid composition such those used in oil and gas operations. The embodiments of this invention are not limited to any particular peroxycarboxylic acid compositions, which can vary and are understood by skilled artisans based on the disclosure herein.

The term "hard surface" refers to a solid, substantially non-flexible surface such as a counter top, tile, floor, wall, panel, window, plumbing fixture, kitchen and bathroom furniture, appliance, engine, circuit board, and dish. Hard surfaces may include for example, health care surfaces and food processing surfaces.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a composition according to the present invention. As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressers, trocars, dilators, cages, glassware, tubing, catheters, cannulas, plugs, stents, scopes (e.g., endoscopes, stethoscopes, and arthroscopes) and related equipment, and the like, or combinations thereof.

The compositions, methods, and kits according to the embodiments of the disclosure provide a very convenient and fast way to quantify peroxycarboxylic acid concentration and are a significant improvement over the prior art. The present disclosure can bring a significant change for industries in need of quantifying peroxycarboxylic acid concentration for effective utilization of the peroxycarboxylic acid compositions and safe release or use of a water source that has been treated with a peroxycarboxylic acid composition. Using the present disclosure, one does not need to collect samples, send them to a properly equipped laboratory, analyze them by highly trained personnel, or use complicated titration procedures that are prone to interference from components present in water. Instead, the present disclosure enables almost anyone to quantify peroxycarboxylic acid concentration in real time and make a decision based on the result. The present kit also improves the overall safety of the procedure by eliminating the need for strong acids and can be easily automated for a real-time estimation of both peroxycarboxylic acid and hydrogen peroxide.

It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present disclosure may be more readily understood, certain terms are first defined. Unless defined otherwise, all technical and scientific terms used herein have the same meaning as commonly understood by one of ordinary skill in the art to which embodiments of the disclosure pertain. Many methods and materials similar, modified, or equivalent to those described herein can be used in the practice of the embodiments of the present disclosure without undue experimentation. The preferred materials and methods are described herein. In describing and claiming the embodiments of the present disclosure, the following terminology will be used in accordance with the definitions set out below.

The term "about," as used herein, refers to variations in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refer to the concentration of those ingredients involved in cleaning expressed as a percentage minus inert ingredients such as water or salts.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods, compositions and kits of the present disclosure may comprise, consist essentially of, or consist of the components and ingredients of the present disclosure as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

Leuco Dye/Redox Sensitive Leuco Dye/Oxidation Sensitive Leuco Dye/Peracid Selective Leuco Dye The compositions, methods, and kits disclosed here include a redox sensitive leuco dye or oxidation sensitive leuco dye. By definition, a leuco dye (from the Greek leukos: white) is a dye that can switch between two chemical forms, one of which is colorless, through either a reversible or irreversible transformation. For example, phenolphthalein is a classic leuco dye that changes color upon a change in pH. Other leuco dyes typically used as redox indicators can be categorized as redox leuco dyes or redox sensitive leuco dyes. Reversible transformation is one caused by heat, light, or pH. Irreversible transformation typically is reduction or oxidation reaction between the redox sensitive leuco dye and another chemical agent.

A redox sensitive/oxidation sensitive leuco dye as used in the present disclosure changes its color by reacting with a peroxycarboxylic acid or a mixture of two or more peroxycarboxylic acids, but not with hydrogen peroxide, when there is no other catalyst for oxidation reaction by peroxycarboxylic acid, peroxide, or hydrogen peroxide present. In other words, a redox sensitive leuco dye as used in the present disclosure is a peracid selective redox sensitive leuco dye. More specifically, the redox sensitive leuco dye used in the present disclosure is an oxidation sensitive leuco dye or a peracid selective leuco dye, as the dye itself is colorless and displays color when oxidized by the peracids.

Suitable redox sensitive leuco dyes for use in the present disclosure are those redox sensitive leuco dyes that are oxidizable dyes and insensitive to hydrogen peroxide. In an aspect, the compositions, methods, and kits disclosed herein include at least one peracid selective dye or one peracid selective redox sensitive leuco dye. Suitable commercially-available peracid selective leuco dyes include TMB (3,3',5, 5'-tetramethylbenzidine, CAS 54827-17-7) and 2,2'-azino-bis (3-ethylbenzothiazoline-6-sulphonic acid (ABTS, CAS 30931-67-0). On the other hand, 4-chloro-naphthol (CAS 604-44-4) and 3-amino-9-ethylcarbazole (CAS 132-32-1) can be used for the estimation of a peroxide or peroxides only in the presence of molybdate and of both peracid/peroxide in the presence of molybdate and iodide.

Peroxycarboxylic Acids (Peracids) and Peroxycarboxylic Acid (Peracid) Compositions As used herein, the terms "mixed" or "mixture" when used relating to "peroxycarboxylic acid composition" refer to a composition or mixture including more than one peroxycarboxylic acid.

As used herein, a peroxycarboxylic acid is usually referred to as a peroxycarboxylic acid compound or substance instead of a peroxycarboxylic acid product or peroxycarboxylic acid composition.

A peroxycarboxylic acid composition or a peroxycarboxylic acid product contains one or more peroxycarboxylic acid compounds and may contain other compounds that ensure the stability or effectiveness of the peroxycarboxylic acid compound(s) as well as the desired pH, viscosity, color, odor, etc. of the final composition or product.

A peroxycarboxylic acid composition or peroxycarboxylic acid product usually is a dynamic equilibrium mixture of one or more peroxycarboxylic acids (such as POAA/PAA, POOA/POA), $H_2O_2$, $H_2O$, and one or more corresponding carboxylic acids. However, as one skilled in the art can ascertain methods of generating peroxycarboxylic acids can also provide non-equilibrium compositions or mixtures. Both equilibrium and non-equilibrium peroxycarboxylic acid composition are suitable for use according to the disclosure.

As used herein, the terms "peroxycarboxylic acid" and "peracid" are used interchangeably and are meant to include chemicals that contain one or more C(O)OOH or C(O)OO⁻ groups. Alternatively, as one of skill in the art appreciates, a peroxycarboxylic acid refers to an acid having the hydrogen of the hydroxyl group in carboxylic acid replaced by a hydroxyl group. Peracids may also be referred to herein as peroxycarboxylic acids.

Sulfoperoxycarboxylic acids, sulfonated peracids and sulfonated peroxycarboxylic acids are also included within the term "peracid" as used herein. The terms "sulfoperoxycarboxylic acid," "sulfonated peracid," or "sulfonated peroxycarboxylic acid" refer to the peroxycarboxylic acid form of a sulfonated carboxylic acid, such as those disclosed in U.S. Pat. No. 8,344,026, and U.S. Patent Publication Nos. 2010/0048730 and 2012/0052134, each of which are incorporated herein by reference in their entirety.

A peracid includes any compound of the formula R—(COOOH)$_n$ in which R can be hydrogen, alkyl, alkenyl, alkyne, acylic, alicyclic group, aryl, heteroaryl, or heterocyclic group, and n is 1, 2, or 3, and named by prefixing the parent acid with peroxy. Preferably R includes hydrogen, alkyl, or alkenyl. The terms "alkyl," "alkenyl," "alkyne," "acylic," "alicyclic group," "aryl," "heteroaryl," and "heterocyclic group" are as defined herein.

As used herein, the term "alkyl" includes a straight or branched saturated aliphatic hydrocarbon chain having from 1 to 22 carbon atoms, such as, for example, methyl, ethyl, propyl, isopropyl (1-methylethyl), butyl, tert-butyl (1,1-dimethylethyl), and the like. The term "alkyl" or "alkyl groups" also refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

Alkenyl groups or alkenes are straight chain, branched, or cyclic alkyl groups having two to about 30 carbon atoms and further including at least one double bond, for example, ethenyl, 1-propenyl, 2-propenyl, 1-butenyl, 2-methyl-1-propenyl, and the like. In some embodiments alkenyl groups have from 2 to about 20 carbon atoms, or typically, from 2 to 10 carbon atoms. Alkenyl groups may be substituted or unsubstituted. Alkenyl groups may be substituted similarly to alkyl groups.

As used herein, the terms "alkylene", "cycloalkylene", "alkynylene" and "alkenylene", alone or as part of another substituent, refer to a divalent radical derived from an alkyl, cycloalkyl, or alkenyl group, respectively, as exemplified by —CH2CH2CH2—. For alkylene, cycloalkylene, alkynylene, and alkenylene groups, no orientation of the linking group is implied.

Alkyl or alkenyl can be terminally substituted with a heteroatom, such as, for example, a nitrogen, sulfur, or oxygen atom, forming an aminoalkyl, oxyalkyl, or thioalkyl, for example, aminomethyl, thioethyl, oxypropyl, and the like. Similarly, the above alkyl or alkenyl can be interrupted in the chain by a heteroatom forming an alkylaminoalkyl, alkylthioalkyl, or alkoxyalkyl, for example, methylaminoethyl, ethylthiopropyl, methoxymethyl, and the like.

Further, as used herein the term "alicyclic" includes any cyclic hydrocarbyl containing from 3 to 8 carbon atoms. Examples of suitable alicyclic groups include cyclopropanyl, cyclobutanyl, cyclopentanyl, etc. The term "heterocyclic" includes any closed ring structures analogous to carbocyclic groups in which one or more of the carbon atoms in the ring is an element other than carbon (heteroatom), for example, a nitrogen, sulfur, or oxygen atom. Heterocyclic groups may be saturated or unsaturated. Examples of suitable heterocyclic groups include for example, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan. Additional examples of suitable heterocyclic groups include groups derived from tetrahydrofurans, furans, thiophenes, pyrrolidines, piperidines, pyridines, pyrrols, picoline, coumaline, etc.

According to the disclosure, alkyl, alkenyl, alicyclic groups, and heterocyclic groups can be unsubstituted or substituted by, for example, aryl, heteroaryl, $C_{1-4}$ alkyl, $C_{1-4}$ alkenyl, $C_{1-4}$ alkoxy, amino, carboxy, halo, nitro, cyano, —SO$_3$H, phosphono, or hydroxy. When alkyl, alkenyl, alicyclic group, or heterocyclic group is substituted, preferably the substitution is C$_{1-4}$ alkyl, halo, nitro, amido, hydroxy, carboxy, sulpho, or phosphono. In one embodiment, R includes alkyl substituted with hydroxy. The term "aryl" includes aromatic hydrocarbyl, including fused aromatic rings, such as, for example, phenyl and naphthyl. The term "heteroaryl" includes heterocyclic aromatic derivatives having at least one heteroatom such as, for example, nitrogen, oxygen, phosphorus, or sulfur, and includes, for example, furyl, pyrrolyl, thienyl, oxazolyl, pyridyl, imidazolyl, thiazolyl, isoxazolyl, pyrazolyl, isothiazolyl, etc. The term "heteroaryl" also includes fused rings in which at least one ring is aromatic, such as, for example, indolyl, purinyl, benzofuryl, etc.

According to the disclosure, aryl and heteroaryl groups can be unsubstituted or substituted on the ring by, for example, aryl, heteroaryl, alkyl, alkenyl, alkoxy, amino, carboxy, halo, nitro, cyano, —SO$_3$H, phosphono, or hydroxy. When aryl, aralkyl, or heteroaryl is substituted, preferably the substitution is C$_{1-4}$ alkyl, halo, nitro, amido, hydroxy, carboxy, sulpho, or phosphono. In one embodiment, R includes aryl substituted with C$_{1-4}$ alkyl.

Peracids suitable for use include any peroxycarboxylic acids, including varying lengths of peroxycarboxylic or percarboxylic acids (e.g. C$_{1-22}$) that can be prepared from the acid-catalyzed equilibrium reaction between a carboxylic acid described above and hydrogen peroxide. A peroxycarboxylic acid can also be prepared by the auto-oxidation of aldehydes or by the reaction of hydrogen peroxide with an acid chloride, acid hydride, carboxylic acid anhydride, or sodium alcoholate. Alternatively, peracids can be prepared through non-equilibrium reactions which may be generated for use in situ, such as the methods disclosed in U.S. Pat. Nos. 8,846,107 and 8,877,254 each titled "In Situ Generation of Peroxycarboxylic Acids at Alkaline pH, and Methods of Use Thereof," US Patent Publication US2016-0176815 A1 titled "Generation of Peroxyformic Acid Through Polyhydric Alcohol Format", US Patent Publication US 2016-0176814 titled "Methods for Forming Peroxyformic Acid and Uses Thereof", U.S. Pat. No. 8,933,263 titled "Water Temperature as a Means of Controlling Kinetics of Onsite Generated Peracids", and U.S. Pat. No. 9,365,509 titled "Continuous On-line Adjustable Disinfectant/Sanitizer/Bleach Generator", all of which are incorporated herein by reference in their entirety. Preferably a composition of the disclosure includes performic acid, peroxyacetic acid, peroxyoctanoic acid, peroxypropionic acid, peroxylactic acid, peroxyheptanoic acid, peroxyoctanoic acid and/or peroxynonanoic acid.

In some embodiments, a peroxycarboxylic acid composition includes at least one water-soluble peroxycarboxylic acid that includes an alkyl group of 1-22 carbon atoms. For example, in one embodiment, a peroxycarboxylic acid composition includes peroxyacetic acid. In another embodiment, a peroxycarboxylic acid composition include one peroxycarboxylic acid that has an alkyl group of 1-22 carbon atoms substituted with one or more hydroxyl groups. Methods of preparing peroxyacetic acid are known to those of skill in the art including those disclosed in U.S. Pat. No. 2,833,813, which is incorporated herein by reference in its entirety.

In another embodiment, a sulfoperoxycarboxylic acid has the following formula:

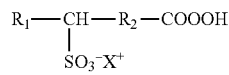

wherein R$_1$ is hydrogen, or a substituted or unsubstituted alkyl group; R$_2$ is a substituted or unsubstituted alkylene group; X is hydrogen, a cationic group, or an ester forming moiety; or salts or esters thereof. In some embodiments, R$_1$ is a substituted or unsubstituted C$_m$ alkyl group; X is hydrogen a cationic group, or an ester forming moiety; R$_2$ is a substituted or unsubstituted C$_n$ alkyl group; m=1 to 10; n=1 to 10; and m+n is less than 18, or salts, esters or mixtures thereof.

In some embodiments, R$_1$ is hydrogen. In other embodiments, R$_1$ is a substituted or unsubstituted alkyl group. In some embodiments, R$_1$ is a substituted or unsubstituted alkyl group that does not include a cyclic alkyl group. In some embodiments, R$_1$ is a substituted alkyl group. In some embodiments, R$_1$ is an unsubstituted C$_1$-C$_9$ alkyl group. In some embodiments, R$_1$ is an unsubstituted C$_7$ or C$_8$ alkyl. In other embodiments, R$_1$ is a substituted C$_8$-C$_{10}$ alkylene group. In some embodiments, R$_1$ is a substituted C$_8$-C$_{10}$ alkyl group substituted with at least 1, or at least 2 hydroxyl groups. In still yet other embodiments, R$_1$ is a substituted C$_1$-C$_9$ alkyl group. In some embodiments, R$_1$ is a substituted C$_1$-C$_9$ alkyl group substituted with at least 1 SO$_3$H group. In other embodiments, R$_1$ is a C$_9$-C$_{10}$ substituted alkyl group. In some embodiments, R$_1$ is a substituted C$_9$-C$_{10}$ alkyl group wherein at least two of the carbons on the carbon backbone form a heterocyclic group. In some embodiments, the heterocyclic group is an epoxide group.

In some embodiments, R$_2$ is a substituted C$_1$-C$_{10}$ alkylene group. In some embodiments, R$_2$ is a substituted C$_8$-C$_{10}$ alkylene. In some embodiments, R$_2$ is an unsubstituted C$_6$-C$_9$ alkylene. In other embodiments, R$_2$ is a C$_8$-C$_{10}$ alkylene group substituted with at least one hydroxyl group. In some embodiments, R$_2$ is a C$_{10}$ alkylene group substituted with at least two hydroxyl groups. In other embodiments, R$_2$ is a C$_8$ alkylene group substituted with at least one SO$_3$H group. In some embodiments, R$_2$ is a substituted C$_9$ group, wherein at least two of the carbons on the carbon backbone form a heterocyclic group. In some embodiments, the heterocyclic group is an epoxide group. In some embodiments, R$_1$ is a C$_8$-C$_9$ substituted or unsubstituted alkyl and R$_2$ is a C$_7$-C$_8$ substituted or unsubstituted alkylene.

These and other suitable sulfoperoxycarboxylic acid compounds for use in the stabilized peroxycarboxylic acid compositions of the disclosure are further disclosed in U.S. Pat. Nos. 8,344,026, 8,809,392, 9,253,978, and 9,359,295 titled "Sulfoperoxycarboxylic Acids, Their Preparation and Methods of Use as Bleaching and Antimicrobial Agents", U.S. Pat. No. 8,425,775 titled "Biofilm Remediation of Fracture Fluid", and U.S. Pat. No. 8,871,807 titled "Detergents Capable of Cleaning, Bleaching, Sanitizing and/or Disinfecting Textiles Including Sulfoperoxycarboxylic Acids", all of which are incorporated herein by reference in their entirety.

In additional embodiments, a sulfoperoxycarboxylic acid is combined with a single or mixed peroxycarboxylic acid composition, such as a sulfoperoxycarboxylic acid with peroxyacetic acid, peroxyoctanoic acid and sulfuric acid (PSOA/POOA/POAA/H$_2$SO$_4$). In other embodiments, a mixed peracid is employed, such as a peroxycarboxylic acid including at least one peroxycarboxylic acid of limited water solubility in which R includes alkyl of 5-22 carbon atoms and at least one water-soluble peroxycarboxylic acid in which R includes alkyl of 1-4 carbon atoms. For example, in one embodiment, a peroxycarboxylic acid includes peroxyacetic acid and at least one other peroxycarboxylic acid such as those named above. Preferably a composition of the disclosure includes peroxyacetic acid and peroxyoctanoic acid. Other combinations of mixed peracids are well suited for use in the current disclosure.

In another embodiment, a mixture of peracetic acid and peroctanoic acid is used to treat a water source, such as disclosed in U.S. Pat. No. 5,314,687 which is herein incorporated by reference in its entirety. In an aspect, the peracid mixture is a hydrophilic peracetic acid and a hydrophobic peroctanoic acid providing antimicrobial synergy. In an aspect, the synergy of a mixed peracid system allows the use of lower dosages of the peracids.

In another embodiment, a tertiary peracid mixture composition, such as peroxysulfonated oleic acid, peracetic acid and peroctanoic acid are used to treat a water source, such as disclosed in U.S. Pat. No. 8,344,026 which is incorporated herein by reference in its entirety. A combination of the three peracids provides significant antimicrobial synergy providing an efficient antimicrobial composition for the water treatment methods according to the disclosure. In addition, it is thought the high acidity built in the composition assists in removing chemical contaminants from the water (e.g. sulfite and sulfide species) and the defoaming agent (e.g. aluminum sulfate) provides defoaming (e.g. combating foam caused by any anionic surface-active agents used in the water treatment).

The mixed peroxycarboxylic acid compositions often provide synergistic micro efficacy. Accordingly, compositions of the disclosure can include a peroxycarboxylic acid, or mixtures thereof.

A peoxycarboxylic acid composition comprising one or more peroxycarboxylic acids is also used in hospitals and clinics, food processing, pharmaceutical, cosmetic, nutritional product plants, hospitality industry, dental, or other health facilities to treat various hard surfaces of instruments, rooms, etc., in order to remove microbes and germs in various forms. For different applications in different settings, the concentration of the peroxycarboxylic acid(s) is a very important factor for consideration for the effective use of the composition and disposal thereof after use.

The desired concentration of the peroxycarboxylic acid(s) in a peroxycarboxylic acid composition of course depends on the purpose of the composition. In some applications in hospitals and clinic, the desired concentration is at least 1,000 ppm to remove biofilm or at least 2,000 ppm to kill spores. In some other applications, the desired concentration can be lower. In some applications, such as in oil and gas operation, the desired concentration is a range of from about 1 ppm to 100 ppm. In any case, use a peroxycarboxylic acid composition in a right way or proper amount to achieve the desired concentration for its intended purpose is critical.

The desired concentration can be obtained from using a ready-to-use product or from diluting a concentrated composition or commercial formulations with a proper amount of water or solvents. However, if one considers the various factors such as product degradation during transportation or storage, consumption during use, or interfering compounds from water or solvents, to decrease peroxycarboxylic acid concentration, real time or on-site checking or monitoring the concentration of the peroxycarboxylic acid(s) before the application of the composition or during the application is always desirable.

Various commercial formulations of peracids are available, including for example peracetic acid (15%) and hydrogen peroxide (10%) available as EnviroSan (Ecolab, Inc., St. Paul Minn.). Most commercial peracid solutions state a specific percarboxylic acid concentration without reference to the other chemical components in a use solution. However, it should be understood that commercial products, such as peracetic acid, will also contain the corresponding carboxylic acid (e.g. acetic acid), hydrogen peroxide and water.

A peroxycarboxylic acid composition of course includes a diluted solution of a concentrated peroxycarboxylic acid, such as a commercially available peracid product. As used here, a peroxycarboxylic acid composition also includes a water source that has been treated with a peroxycarboxylic acid composition, since after treatment, the water source contains a peroxycarboxylic acid.

When a peroxycarboxylic acid composition or water source contains two or more peroxycarboxylic acids, the compositions, methods, and kits disclosed herein can be used for quantifying the total concentration of the peroxycarboxylic acids in the same peroxycarboxylic acid composition or the water source.

Water Sources

As used here, a water source is any body of water that has been treated or contacted with a peroxycarboxylic acid, peroxycarboxylic acid composition, or peroxycarboxylic acid product. In some embodiments, the water source used in the present disclosure is a diluted peroxycarboxylic acid composition. In some other embodiments, the water source used in the present disclosure is a water source previously treated with a peroxycarboxylic acid composition. In some embodiments, the water source or the peroxycarboxylic acid composition is a solution ready for treating instrument surfaces or walls of room, or a resulted solution after such treatments. In some embodiments, the water source or the peroxycarboxylic acid composition may be subjected to additional treatments before or after its formation.

As one skilled in the art will ascertain, a peroxycarboxylic acid composition has been used in treatment of all kinds of water sources, such as dormant water sources and flow back waters. Usually, peracid use solutions are added to waters in need of treatment. For example, a water source is treated by a peracid composition before its disposal. Flow back waters (e.g. post fracking) are treated to minimize microbial contaminations in the waters and to remove solids prior to disposal of the water into a subterranean well, reuse in a subsequent fracturing application or return of the water into local environmental water sources. Such flow back waters may be held, for example, in tanks, ponds or the like.

In an aspect, the water source in need of treatment may vary significantly. In one example, the water source is the water used in a food or beverage plant. In another example, the water source may be a freshwater source (e.g. pond water), salt water or brine source, brackish water source, recycled water source, or the like used in other industries. In an aspect, wherein offshore well drilling operations are involved, sea water sources are often employed (e.g. saltwater or non-saltwater). Beneficially, the composition, methods, and kits include or are suitable for use with any types of water and provide effective quantification of peroxycarboxylic acid with any of such water sources.

Large volumes of water are required in oil and gas operations. As a result, in an aspect of the disclosure, recycled water sources (e.g. produced waters) are often employed to reduce the amount of a freshwater, pond water or sea water source required. Recycled or produced water are understood to include non-potable water sources. The use of such produced waters (in combination with freshwater, pond water or sea water) reduces certain economic and/or environmental constraints. In an aspect of the disclosure, thousands to millions of gallons of water may be employed and the combination of produced water with fresh water sources provides significant economic and environmental advantages.

It is the large volumes of water required in oil and gas operations and stored in ponds, underground reservoirs, or the like whose volume is almost impossible to measure or estimate, that makes the present disclosure valuable because accurate quantification of peracid could save a lot of money and reduce harm to environment and equipment. With the present disclosure, one does not have to treat a water source to an unnecessary higher level of peroxycarboxylic acid(s) or to release a water source with a harmful level of peracid as well.

In some aspects, a water source may go through a pretreatment or post-treatment step as well. For example, a peracid composition is treated with a peroxide-reducing agent to reduce the hydrogen peroxide concentration in a use solution before the peracid composition is applied to a water source. Or in some other situations, the water source itself is treated with a peroxide-reducing agent to reduce the hydrogen peroxide concentration after a peroxycarboxylic acid is applied. Thereafter, the water source or peroxycarboxylic acid composition may contain the desired peracetic acid concentrations, but with low and/or no hydrogen peroxide concentration.

In some aspects, a water source or peroxycarboxylic acid composition is a composition for disinfection and simultaneous decontamination of objects contaminated by conventional transmissible agents (ATC), such as including bacteria, yeast, viruses, mold spores, mycobacteria, bacteria spore, and non-transmissible agents conventional (NCTA) such as prions. An object, such as endoscope or other surgical device/equipment/instrument in hospitals and clinics, may be contaminated by a TAC and/or NCTA, following its contact with certain human or animal organs and/or body fluids. For this type of applications, the peroxycarboxylic acid compositions may contain up to 0.09 wt-% of one or more peroxycarboxylic acids. These peroxycarboxylic acid compositions may also contain up to 0.0108 wt-% of one or more copper salts and other salts.

In some aspects, the desired peroxycarboxylic acid concentration in a water source or peroxycarboxylic acid composition needs to remain above 1,000 ppm or above 2,000 ppm to be effective.

In some situations, a sufficient amount of the peroxycarboxylic acid composition in the use solution is added to the aqueous water source in need of treatment to provide the desired peracid concentration for antimicrobial efficacy. For example, a water source is dosed amounts of the peracid until a peracid concentration within the water source is detected within the preferred concentration range (e.g. about 1 ppm to about 100 ppm peracid). In some other situations, after the water source is dosed with sufficient peroxycarboxylic acid, a reducing agent, such as a catalase enzyme or an agent with higher oxidative potential, is introduced to the water source to reduce hydrogen peroxide or peracid concentration. In some other situations, an additional agent may be added to a water source to block the UV light or slow down the breakage of hydrogen peroxide or peroxycarboxylic acid.

In some embodiments of the present disclosure, a water source or peroxycarboxylic acid composition may be pretreated or processed, such as diluted, filtered, discolored, pH adjusted, before the water source or peroxycarboxylic acid composition is used to make the claimed composition. For example, dilution of the water source or using reduced amount of the water source and additional amount of water or other solvents is necessary to make the estimated concentration of the peracid(s) in the peroxycarboxylic acid quantification composition fall between 1 ppm and 100 ppm in order to give an accurate concentration measurement.

Peroxycarboxylic Acid (Peracid) Quantification Compositions

In one aspect, the present disclosure provides a peroxycarboxylic acid quantification composition. The composition comprises a redox sensitive leuco dye and a peroxycarboxylic acid composition; wherein the peroxycarboxylic acid composition comprises a $C_1$-$C_{22}$ peroxycarboxylic acid, the redox sensitive leuco dye selectively reacts with the peroxycarboxylic acid in the peroxycarboxylic acid composition to form a colored species, the redox sensitive leuco dye does not react with hydrogen peroxide, and the colored species exhibits a stable absorbance within about 20 minutes at a visible light wavelength and the absorbance intensity linearly proportional to the concentration of the peroxycarboxylic acid of between about 1 ppm and about 100 ppm. As used in this disclosure, the phrase "the redox sensitive leuco dye selectively reacts with the peroxycarboxylic acid" means that the redox sensitive leuco dye reacts with a peroxycarboxylic acid, but not with hydrogen peroxide.

In some embodiments, the redox sensitive leuco dye in the peroxycarboxylic acid quantification composition has a concentration of from about 30 ppm to about 1000 ppm, from about 30 ppm to about 50 ppm, from about 30 ppm to about 100 ppm, from about 30 ppm to about 200 ppm, from about 30 ppm to about 300 ppm, from about 30 ppm to about 400 ppm, from about 30 ppm to about 500 ppm, from about 30 ppm to about 600 ppm, from about 30 ppm to about 700 ppm, from about 30 ppm to about 800 ppm, from about 30 ppm to about 900 ppm, from about 50 ppm to about 100 ppm, from about 30 ppm to about 100 ppm, from about 50 ppm to about 200 ppm, from about 50 ppm to about 300 ppm, from about 50 ppm to about 400 ppm, from about 50 ppm to about 500 ppm, from about 50 ppm to about 600 ppm, from about 50 ppm to about 700 ppm, from about 50 ppm to about 800 ppm, from about 50 ppm to about 900 ppm, from about 50 ppm to about 1000 ppm, from about 100 ppm to about 200 ppm, from about 100 ppm to about 300 ppm, from about 100 ppm to about 400 ppm, from about 100 ppm to about 500 ppm, from about 100 ppm to about 600 ppm, from about 100 ppm to about 700 ppm, from about 100 ppm to about 800 ppm, from about 100 ppm to about 900 ppm, from about 100 ppm to about 1000 ppm, from about 150 ppm to about 300 ppm, from about 150 ppm to about 400 ppm, from about 150 ppm to about 500 ppm, from about 150 ppm to about 600 ppm, from about 150 ppm to about 700 ppm, from about 150 ppm to about 800 ppm, from about 150 ppm to about 900 ppm, from about 150 ppm to about 1000 ppm, from about 200 ppm to about 300 ppm, from about 200 ppm to about 400 ppm, from about 200 ppm to about 500 ppm, from about 200 ppm to about 600 ppm, from about 200 ppm to about 700 ppm, from about 200 ppm to about 800 ppm, from about 200 ppm to about 900 ppm, from about 200 ppm to about 1000 ppm, from about 300 ppm to about 400 ppm, from about 300 ppm to about 500 ppm, from about 300 ppm to about 600 ppm, from about 300 ppm to about 700 ppm, from about 300 ppm to about 800 ppm, from about 300 ppm to about 900 ppm, from about 300 ppm to about 1000 ppm, from about 400 ppm to about 500 ppm, from about 400 ppm to about 600 ppm, from about 400 ppm to about 700 ppm, from about 400 ppm to about 800 ppm, from about 400 ppm to about 900 ppm, from about 400 ppm to about 1000 ppm, from about 500 ppm to about 600 ppm, from about 500 ppm to about 700 ppm, from about 500 ppm to about 800 ppm, from about 500 ppm to about 900 ppm, from about 500 ppm to about 1000 ppm, from about 600 ppm to about 700 ppm, from about 600 ppm to about 800 ppm, from about 600 ppm to about 900 ppm, from about 600 ppm to about 1000 ppm, from about 700 ppm to about 800 ppm, from about 700 ppm to about 900 ppm, from about 700 ppm to about 1000 ppm, from about 800 ppm to about 900 ppm, from about 800 ppm to about 1000 ppm, or from about 900 ppm to about 1000 ppm.

In some embodiments, the redox sensitive leuco dye in the peroxycarboxylic acid quantification composition has a concentration of about 30 ppm, about 40 ppm, about 50 ppm, about 80 ppm, about 100 ppm, about 150 ppm, about 200 ppm, about 250 ppm, about 300 ppm, about 350 ppm, about 450 ppm, about 500 ppm, about 550 ppm, about 600 ppm, about 650 ppm, about 700 ppm, about 750 ppm, about 800 ppm, about 850 ppm, about 900 ppm, about 950 ppm, about 1000 ppm, or any value there between.

In some other embodiments, the quantification composition is free of iodide or any other catalysts for the oxidation of the redox sensitive leuco dye, such as molybdate.

In some other embodiments, the peroxycarboxylic acid composition further comprises hydrogen peroxide, a $C_1$-$C_{22}$ carboxylic acid, or combination thereof.

In some embodiments, the peroxycarboxylic acid composition is a diluted antimicrobial peroxycarboxylic acid composition including a water source selected from the group consisting of fresh water, pond water, sea water, produced water, and combination thereof, wherein the fresh water, pond water, sea water, produced water, or a combination thereof has been treated previously with an antimicrobial peroxycarboxylic acid composition. In some other embodiments, the peroxycarboxylic acid composition is a water source previously treated with an antimicrobial peroxycarboxylic acid composition.

In some embodiments, the peroxycarboxylic acid composition is a diluted antimicrobial peroxycarboxylic acid composition.

In some embodiments, the peroxycarboxylic acid composition in the peroxycarboxylic acid quantification composition comprises peroxyformic acid. In some other embodiments, the peroxycarboxylic acid composition comprises peroxyacetic acid. In yet some other embodiments, the peroxycarboxylic acid composition comprises a $C_1$-$C_{22}$, $C_1$-$C_2$, $C_3$-$C_6$, $C_7$-$C_{12}$, $C_{13}$-$C_{18}$, or $C_{18}$-$C_{22}$ peroxycarboxylic acid. In yet other embodiments, the peroxycarboxylic acid composition comprises a combination of $C_1$-$C_{22}$ peroxycarboxylic acids, or a $C_1$-$C_{22}$ peroxycarboxylic acid and a persulfonated carboxylic acid.

In some embodiments, the concentration of the peroxycarboxylic acid in the peroxycarboxylic acid composition is from about 1 ppm to about 100 ppm, from about 1 ppm to about 5 ppm, from about 1 ppm to about 10 ppm, from about 1 ppm to about 20 ppm, from about 1 ppm to about 30 ppm, from about 1 ppm to about 40 ppm, from about 1 ppm to about 50 ppm, from about 1 ppm to about 60 ppm, from about 1 ppm to about 70 ppm, from about 1 ppm to about 80 ppm, from about 1 ppm to about 90 ppm, from about 1 ppm to about 100 ppm, from about 5 ppm to about 10 ppm, from about 5 ppm to about 20 ppm, from about 5 ppm to about 30 ppm, from about 5 ppm to about 40 ppm, from about 5 ppm to about 50 ppm, from about 5 ppm to about 60 ppm, from about 5 ppm to about 70 ppm, from about 5 ppm to about 80 ppm, from about 5 ppm to about 90 ppm, from about 5 ppm to about 100 ppm, from about 10 ppm to about 20 ppm, from about 10 ppm to about 30 ppm, from about 10 ppm to about 40 ppm, from about 10 ppm to about 50 ppm, from about 10 ppm to about 60 ppm, from about 10 ppm to about 70 ppm, from about 10 ppm to about 80 ppm, from about 10 ppm to about 90 ppm, from about 10 ppm to about 100 ppm, from about 15 ppm to about 30 ppm, from about 15 ppm to about 40 ppm, from about 15 ppm to about 50 ppm, from about 15 ppm to about 60 ppm, from about 15 ppm to about 70 ppm, from about 15 ppm to about 80 ppm, from about 15 ppm to about 90 ppm, from about 15 ppm to about 100 ppm, from about 20 ppm to about 30 ppm, from about 20 ppm to about 40 ppm, from about 20 ppm to about 50 ppm, from about 20 ppm to about 60 ppm, from about 20 ppm to about 70 ppm, from about 20 ppm to about 80 ppm, from about 20 ppm to about 900 ppm, from about 20 ppm to about 100 ppm, from about 30 ppm to about 40 ppm, from about 30 ppm to about 50 ppm, from about 30 ppm to about 60 ppm, from about 30 ppm to about 70 ppm, from about 30 ppm to about 80 ppm, from about 30 ppm to about 90 ppm, from about 30 ppm to about 100 ppm, from about 40 ppm to about 50 ppm, from about 40 ppm to about 60 ppm, from about 40 ppm to about 70 ppm, from about 40 ppm to about 80 ppm, from about 40 ppm to about 90 ppm, from about 40 ppm to about 100 ppm, from about 50 ppm to about 60 ppm, from about 50 ppm to about 70 ppm, from about 50 ppm to about 80 ppm, from about 50 ppm to about 90 ppm, from about 50 ppm to about 100 ppm, from about 60 ppm to about 70 ppm, from about 60 ppm to about 80 ppm, from about 60 ppm to about 90 ppm, from about 60 ppm to about 100 ppm, from about 70 ppm to about 80 ppm, from about 70 ppm to about 90 ppm, from about 70 ppm to about 100 ppm, from about 80 ppm to about 90 ppm, from about 80 ppm to about 100 ppm, or from about 90 ppm to about 100 ppm.

In some embodiments, the concentration of the peroxycarboxylic acid in the peroxycarboxylic acid composition is about 1 ppm, about 3 ppm, about 4 ppm, about 5 ppm, about 8 ppm, about 10 ppm, about 15 ppm, about 20 ppm, about 25 ppm, about 30 ppm, about 35 ppm, about 45 ppm, about 50 ppm, about 55 ppm, about 60 ppm, about 65 ppm, about 70 ppm, about 75 ppm, about 80 ppm, about 85 ppm, about 90 ppm, about 95 ppm, about 100 ppm, or any value there between.

In some embodiments, the concentration of the peroxycarboxylic acid in the peroxycarboxylic acid composition is at least 1,000 ppm, at least 2,000 ppm, from about 100 ppm to about 3,000 ppm, from about 100 ppm to about 2,500 ppm, from about 100 ppm to about 2,000 ppm, from about 100 ppm to about 1,500 ppm, from about 100 ppm to about 1,000 ppm, from about 100 ppm to about 900 ppm, from about 100 ppm to about 800 ppm, from about 100 ppm to about 700 ppm, from about 100 ppm to about 600 ppm, from about 100 ppm to about 500 ppm, from about 100 ppm to about 400 ppm, from about 100 ppm to about 300 ppm, from about 100 ppm to about 200 ppm, about 150 ppm, about 200 ppm, about 250 ppm, about 300 ppm, about 350 ppm, about 400 ppm, about 450 ppm, about 500 ppm, about 600 ppm, about 650 ppm, about 700 ppm, about 750 ppm, about 800 ppm, about 900 ppm, about 1000 ppm, about 1,100 ppm, about 1,200 ppm, about 1,300 ppm, about 1,400 ppm, about 1,500 ppm, about 1,600 ppm, about 1,700 ppm, about 1,800 ppm, about 1,900 ppm, about 2,000 ppm, about 2,200 ppm, about 2,400 ppm, about 2,600 ppm, about 2,800 ppm, about 3,000 ppm, or any value there between.

If the concentration of the peroxycarboxylic acid in the peroxycarboxylic acid composition is high, for example, above 100 ppm or above 200 ppm, either a reduced amount of the composition or dilution of the composition is necessary to make the final concentration of the peroxycarboxylic acid(s) in the peroxycarboxylic acid quantification composition fall in between 1 ppm and 100 ppm. One skilled in the art knows how to use water or other solvent together with using reduced amount of the original peroxycarboxylic acid composition to achieve the desired concentration of from about 1 ppm to about 100 ppm in the final peroxycarboxylic acid quantification composition. One skilled in the art also knows how to use two or more different dilutions to make sure the peroxycarboxylic acid concentration in the final peroxycarboxylic acid quantification composition is indeed within the 1 ppm to 100 ppm range.

In some embodiments, the concentration of the peroxycarboxylic acid in the peroxycarboxylic acid composition is diluted from a higher concentration to a concentration of from about 1 ppm to about 100 ppm. The dilution of the peroxycarboxylic acid is through adding more water or other solvent to the peroxycarboxylic acid or adding reduced amount of the peroxycarboxylic acid composition and additional amount of water or other solvents.

In some embodiments, the quantification composition has a pH of from about 2 to about 9, from about 3 to about 5, about 3, about 3.5, about 2, about, 3, about 4, about 5, about 6, about 7, about 8, about 9, or any value there between. In some other embodiments, the composition has a pH of from about 2 to about 3, from about 3 to about 4, from about 4 to about 5, from about 5 to about 7, from about 7 to about 9, from about 2 to about 5, from about 5 to about 9, or any value there between.

In some embodiments, the redox sensitive leuco dye is a benzidine or benzidine derivatives. In some other embodiments, the redox sensitive leuco dye is 3,3',5,5'-tetramethylbenzidine (TMB).

In some embodiments, the visible light wavelength is from about 400 nm to about 700 nm, about 400 nm, about 440 nm, about 460 nm, about 480 nm, about 500 nm, about 520 nm, about 540 nm, about 560 nm, about 580 nm, about 600 nm, about 620 nm, about 640 nm, about 660 nm, about 680 nm, about 700 nm, or any value there between.

In some embodiments, the visible light wavelength is about 424 nm.

In some embodiments, the quantification composition is resulted from simply mixing the leuco dye with the peroxycarboxylic acid composition or a porting of the peroxycarboxylic acid composition for which the peroxycarboxylic acid concentration need to be measured. In some other embodiments, the quantification composition is resulted from mixing the redox sensitive leuco dye with a pretreated peroxycarboxylic acid composition. The pretreated peroxycarboxylic acid composition is a result of diluting, de-coloring, pH adjusting, or other common conditioning of the original peroxycarboxylic acid composition or a portion of the original peroxycarboxylic acid composition.

In some embodiments, the redox sensitive leuco dye is a solid when it mixes with the peroxycarboxylic acid composition or a portion of the peroxycarboxylic acid composition. In some other embodiments, the redox sensitive leuco dye is in a solvent. In some embodiments, the redox sensitive leuco dye is in a solid state when it mixes with the peroxycarboxylic acid composition or a portion of the peroxycarboxylic acid composition. In some other embodiments, the redox sensitive leuco dye is dissolved in water or a solvent.

In some embodiments, the peroxycarboxylic acid quantification composition further comprises other chemical agents for adjusting or maintaining pH of the composition (agent for pH buffering). Agents used for adjusting pH include but are not limited to bicarbonate, acetates, phosphates, tris (tris(hydroxymethyl)aminomethane) salts, HEPES (4-(2-hydroxyethyl)-1-piperazineethanesulfonic acid), and etc.

In practice, a peroxycarboxylic acid quantification composition is formed by mixing a composition comprising the redox sensitive leuco dye with a sample taken from the water source or peroxycarboxylic acid composition, with or without addition of water or other solvents. The composition comprising the redox sensitive leuco dye can be a solid mixture or liquid solution.

For example, in a vial containing a solid composition comprising the redox sensitive leuco dye and having a set 10 mL volume mark, one can add 10 mL of the water source or peroxycarboxy acid composition to the 10 mL volume mark to form the peroxycarboxylic acid quantification composition. In this case, the measured concentration for peroxycarboxylic acid reflects the peroxycarboxylic acid concentration in the water source or peroxycarboxylic acid composition. In another situation, one can add 1 mL of the water source into a similar vial, then add water to the 10 mL volume mark to form the peroxycarboxylic acid quantification composition. In this situation, the measured concentration is 1/10 of the concentration of the peroxycarboxylic acid in the original water source. In this way, a concentration of from about 10 ppm to 1,000 ppm can be measured accurately. In a similar fashion, higher concentration of more than 1,000 ppm can be measured as well.

Method of Quantifying a Peroxycarboxylic Acid Concentration in a Treated Water Source In another aspect, the present disclosure provides a method of quantifying a peroxycarboxylic acid concentration in a treated water source. The method comprises providing a water source or a sample of a water source, contacting the water source with a redox sensitive leuco dye to form a peroxycarboxylic acid quantification composition, and measuring an absorbance of the peroxycarboxylic acid quantification composition at a visible light wavelength to quantify the peroxycarboxylic acid by using the absorbance-peroxycarboxylic acid concentration standard curve or by comparing the color of the peroxycarboxylic acid quantification against a color-peroxycarboxylic acid concentration chart; wherein the water source comprises a $C_1$-$C_{22}$ peroxycarboxylic acid, a $C_1$-$C_{22}$ carboxylic acid, hydrogen peroxide, or a combination thereof.

In some embodiments, the method further comprises pretreating, de-coloring, diluting, or a combination thereof of the water source before its contact with the redox sensitive leuco dye.

In some embodiments, the water source is selected from fresh water, pond water, sea water, produced water, and combinations thereof. In some other embodiments, the water source is a peroxycarboxylic acid composition.

In some embodiments, the leuco dye is solid when it contacts with the water source or pretreated water source. In some other embodiments, the leuco dye is in a solvent. In some other embodiments, the solvent is an alcohol, water, a ketone, ether or mixture thereof.

For the present disclosure, the step of contacting the water source with a dye is not a titration process during which the contacting of the water source is done in a multiple step fashion.

In some embodiments, the water source comprises peroxyformic acid. In some other embodiments, the water comprises peroxyacetic acid. In yet another embodiment, the water source comprises a $C_3$-$C_{18}$, $C_3$-$C_6$, $C_7$-$C_{12}$, $C_{13}$-$C_{18}$, or $C_{18}$-$C_{22}$ peroxycarboxylic acid. In yet other embodiments, the peroxycarboxylic acid composition comprises a combination of $C_1$-$C_{22}$ peroxycarboxylic acids, or a $C_1$-$C_{22}$ peroxycarboxylic acid and a persulfonated carboxylic acid.

In some embodiments, the peroxycarboxylic acid in the water source is from about 1 ppm to about 100 ppm, from about 1 ppm to about 5 ppm, from about 1 ppm to about 10 ppm, from about 1 ppm to about 20 ppm, from about 1 ppm to about 30 ppm, from about 1 ppm to about 40 ppm, from about 1 ppm to about 50 ppm, from about 1 ppm to about 60 ppm, from about 1 ppm to about 70 ppm, from about 1 ppm to about 80 ppm, from about 1 ppm to about 90 ppm, from about 1 ppm to about 100 ppm, from about 5 ppm to about 10 ppm, from about 5 ppm to about 20 ppm, from about 5 ppm to about 30 ppm, from about 5 ppm to about 40 ppm, from about 5 ppm to about 50 ppm, from about 5 ppm to about 60 ppm, from about 5 ppm to about 70 ppm, from about 5 ppm to about 80 ppm, from about 5 ppm to about 90 ppm, from about 5 ppm to about 100 ppm, from about 10 ppm to about 20 ppm, from about 10 ppm to about 30 ppm, from about 10 ppm to about 40 ppm, from about 10 ppm to about 50 ppm, from about 10 ppm to about 60 ppm, from about 10 ppm to about 70 ppm, from about 10 ppm to about 80 ppm, from about 10 ppm to about 90 ppm, from about 10 ppm to about 100 ppm, from about 15 ppm to about 30 ppm, from about 15 ppm to about 40 ppm, from about 15 ppm to about 50 ppm, from about 15 ppm to about 60 ppm, from about 15 ppm to about 70 ppm, from about 15 ppm to about 80 ppm, from about 15 ppm to about 90 ppm, from about 15 ppm to about 100 ppm, from about 20 ppm to about 30 ppm, from about 20 ppm to about 40 ppm, from about 20 ppm to about 50 ppm, from about 20 ppm to about 60 ppm, from about 20 ppm to about 70 ppm, from about 20 ppm to about 80 ppm, from about 20 ppm to about 900 ppm, from about 20 ppm to about 100 ppm, from about 30 ppm to about 40 ppm, from about 30 ppm to about 50 ppm, from about 30 ppm to about 60 ppm, from about 30 ppm to about 70 ppm, from about 30 ppm to about 80 ppm, from about 30 ppm to about 90 ppm, from about 30 ppm to about 100 ppm, from about 40 ppm to about 50 ppm, from about 40 ppm to about 60 ppm, from about 40 ppm to about 70 ppm, from about 40 ppm to about 80 ppm, from about 40 ppm to about 90 ppm, from about 40 ppm to about 100 ppm, from about 50 ppm to about 60 ppm, from about 50 ppm to about 70 ppm, from about 50 ppm to about 80 ppm, from about 50 ppm to about 90 ppm, from about 50 ppm to about 100 ppm, from about 60 ppm to about 70 ppm, from about 60 ppm to about 80 ppm, from about 60 ppm to about 90 ppm, from about 60 ppm to about 100 ppm, from about 70 ppm to about 80 ppm, from about 70 ppm to about 90 ppm, from about 70 ppm to about 100 ppm, from about 80 ppm to about 90 ppm, from about 80 ppm to about 100 ppm, or from about 90 ppm to about 100 ppm.

In some embodiments, the concentration of the peroxycarboxylic acid in the water is about 1 ppm, about 3 ppm, about 4 ppm, about 5 ppm, about 8 ppm, about 10 ppm, about 15 ppm, about 20 ppm, about 25 ppm, about 30 ppm, about 35 ppm, about 45 ppm, about 50 ppm, about 55 ppm, about 60 ppm, about 65 ppm, about 70 ppm, about 75 ppm, about 80 ppm, about 85 ppm, about 90 ppm, about 95 ppm, about 100 ppm, or any value there between.

In some embodiments, the concentration of the peroxycarboxylic acid in the peroxycarboxylic acid composition is at least 1,000 ppm, at least 2,000 ppm, from about 100 ppm to about 3,000 ppm, from about 100 ppm to about 2,500 ppm, from about 100 ppm to about 2,000 ppm, from about 100 ppm to about 1,500 ppm, from about 100 ppm to about 1,000 ppm, from about 100 ppm to about 900 ppm, from about 100 ppm to about 800 ppm, from about 100 ppm to about 700 ppm, from about 100 ppm to about 600 ppm, from about 100 ppm to about 500 ppm, from about 100 ppm to about 400 ppm, from about 100 ppm to about 300 ppm, from about 100 ppm to about 200 ppm, about 150 ppm, about 200 ppm, about 250 ppm, about 300 ppm, about 350 ppm, about 400 ppm, about 450 ppm, about 500 ppm, about 600 ppm, about 650 ppm, about 700 ppm, about 750 ppm, about 800 ppm, about 900 ppm, about 1000 ppm, about 1,100 ppm, about 1,200 ppm, about 1,300 ppm, about 1,400 ppm, about 1,500 ppm, about 1,600 ppm, about 1,700 ppm, about 1,800 ppm, about 1,900 ppm, about 2,000 ppm, about 2,200 ppm, about 2,400 ppm, about 2,600 ppm, about 2,800 ppm, about 3,000 ppm, or any value there between.

In some embodiments, the concentration of the peroxycarboxylic acid in the water source is diluted from a higher concentration to a concentration of from about 1 ppm to about 100 ppm in the peroxycarboxylic acid quantification composition. The dilution of the peroxycarboxylic acid is through adding more water or other solvent to the peroxycarboxylic acid.

Alternatively, taking less amount of the water source and more water or solvents to form the peroxycarboxylic acid quantification composition enables the measurement of a peracid concentration greater than 100 ppm. For example, taking 10 μL of the water source to make a 10 mL peroxycarboxylic acid quantification composition, the measured peroxycarboxylic acid concentration would be $\frac{1}{1,000}$ of the concentration in the water source. Accordingly, taking 100 μL of the water source to make a 10 mL peroxycarboxylic acid quantification composition, the measured peroxycarboxylic acid concentration would be $\frac{1}{100}$ of the concentration in the water source.

In some embodiments, the redox sensitive leuco dye is a benzidine, bezidine derivative, or 3,3',5,5'-tetramethylbenzidine (TMB).

Colorimetric Assay Kits

In yet another aspect, the present disclosure provides a colorimetric assay kit. The kit comprises a clear and colorless vial containing a redox sensitive leuco dye and a color—peroxycarboxylic acid concentration chart; wherein the vial can receive a certain amount of a peroxycarboxylic acid composition.

In some embodiments, the redox sensitive leuco dye is a solid. In some other embodiments, the redox sensitive leuco dye is in a solvent. In some embodiments, the solvent is an alcohol, water, a ketone, ether or mixture thereof. In some other embodiments, the solvent is a mixture of water and ethanol.

In some other embodiments, the kit is free of iodide or any other catalysts for the oxidation of the redox sensitive leuco dye, such as molybdate.

In some embodiments, the kit further comprises other chemical agent(s) for adjusting or maintaining pH, such as bicarbonate and other pH adjustment agents to buffer the range of 4-10, in the vial.

In some embodiments, the vial has a volume of from about 3 mL to about 50 mL. In other embodiments, the redox sensitive leuco dye in the vial has a weight from about 0.03 mg to about 1 g, from about 0.03 mg to about 1 mg, from about 0.03 mg to about 10 mg, from about 0.03 mg to about 100 mg, or any value there between.

All publications and patent applications in this specification are indicative of the level of ordinary skill in the art to which this disclosure pertains. All publications and patent applications are herein incorporated by reference to the same extent as if each individual publication or patent application was specifically and individually indicated as incorporated by reference.

EXAMPLES

Embodiments of the present disclosure are further defined in the following non-limiting Examples. It should be understood that these Examples, while indicating certain embodiments of the disclosure, are given by way of illustration only. From the above discussion and these Examples, one skilled in the art can ascertain the essential characteristics of this disclosure, and without departing from the spirit and scope thereof, can make various changes and modifications of the embodiments of the disclosure to adapt it to various usages and conditions. Thus, various modifications of the embodiments of the disclosure, in addition to those shown and described herein, will be apparent to those skilled in the art from the foregoing description. Such modifications are also intended to fall within the scope of the appended claims.
Materials 0.1535 g of Tetramethyl benzidine was dissolved in 20 ml of 95% Ethanol. The mixture was diluted with water to 500 mL. A peroxycarboxylic acid composition (15% peracetic acid and 10% peroxide) was used for peroxycarboxylic acid concentration estimation. Formic acid was used as the acid and hydrogen peroxide (35%) was used as a source of peroxide.
Time Course of Absorbance Measurements
For absorbance measurements experiments 3 mL of the dye prepared above was used. 5 µL of the peroxycarboxylic acid product was used. The absorbance was monitored using wavelength scan between 200 to 800 nm in time intervals shown below.

Example 1

Time Course of Absorbance Measurements
For absorbance measurements experiments 3 mL of the dye prepared above was used. 5 µL of the peroxycarboxylic acid product was used. The absorbance was monitored using wavelength scan between 200 to 800 nm in time intervals as shown in FIG. 1. Table 1 lists the absorbance values at 424 nm and 326 nm, respectively, at different times.

TABLE 1

|  | Time (minutes) | | | | | |
| --- | --- | --- | --- | --- | --- | --- |
|  | 0.5 | 2.5 | 5 | 10 | 15 | 20 |
| Absorbance at 424 nm | 0.076664 | 0.237695 | 0.394483 | 0.562642 | 0.633412 | 0.703008 |
| Absorbance at 424 nm | 0.121822 | 0.197992 | 0.287249 | 0.493901 | 0.755197 | 0.966646 |

As can be seen in FIG. 1, the absorbance features show two distinct peaks. One at 424 nm and another at 326 nm. It should also be noted that the absorbance peaks increased as a function of time. After 20 minutes the absorbance at 424 nm stabilized and did not show a significant increase. For quantitative measurements, this data indicates the time period of incubation is critical.

Figure 2:
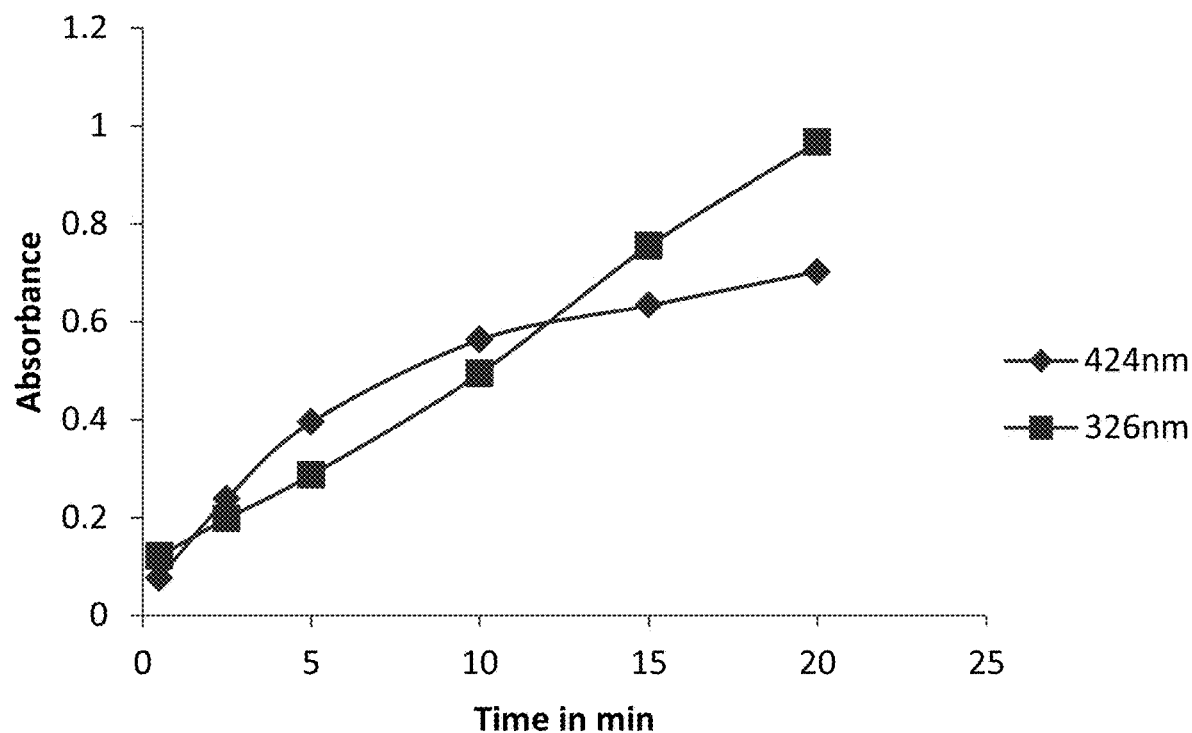
FIG. 2 shows the absorbance of the mixture of peracetic acid composition and 3,3',5,5'-tetramethylbenzidine (TMB) at 326 nm and 424 nm, respectively, at different times after the mixture formation.

The peak absorbances measured at 424 nm and 326 nm are also plotted as a function of time in FIG. 2. As can be seen in FIG. 2, the absorbance at 424 nm brings to saturate/taper while the absorbance measurement at 326 nm continues to increase. It may be beneficial to monitor absorbances at 424 nm instead of 326 nm for the purposes of quantitation of peroxycarboxylic acids and peroxide.

Figure 3A:
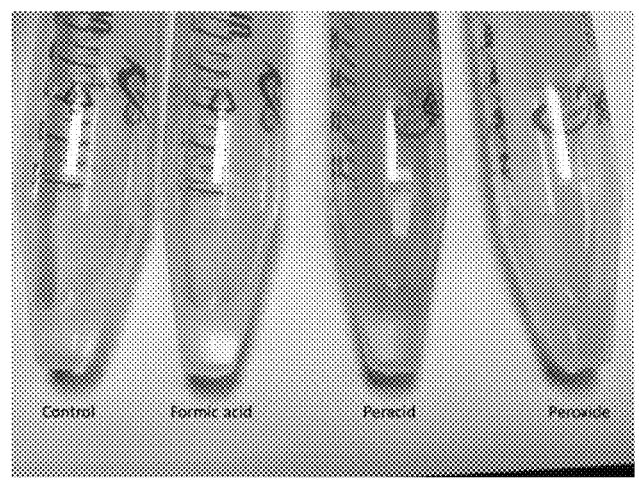
FIG. 3A shows color formations observed upon addition of peracetic acid composition, hydrogen peroxide alone, water alone, or formic acid alone to 3,3',5,5'-tetramethylbenzidine (TMB) solution. No color change is observed with water, acid, or hydrogen peroxide addition.
Figure 3B:
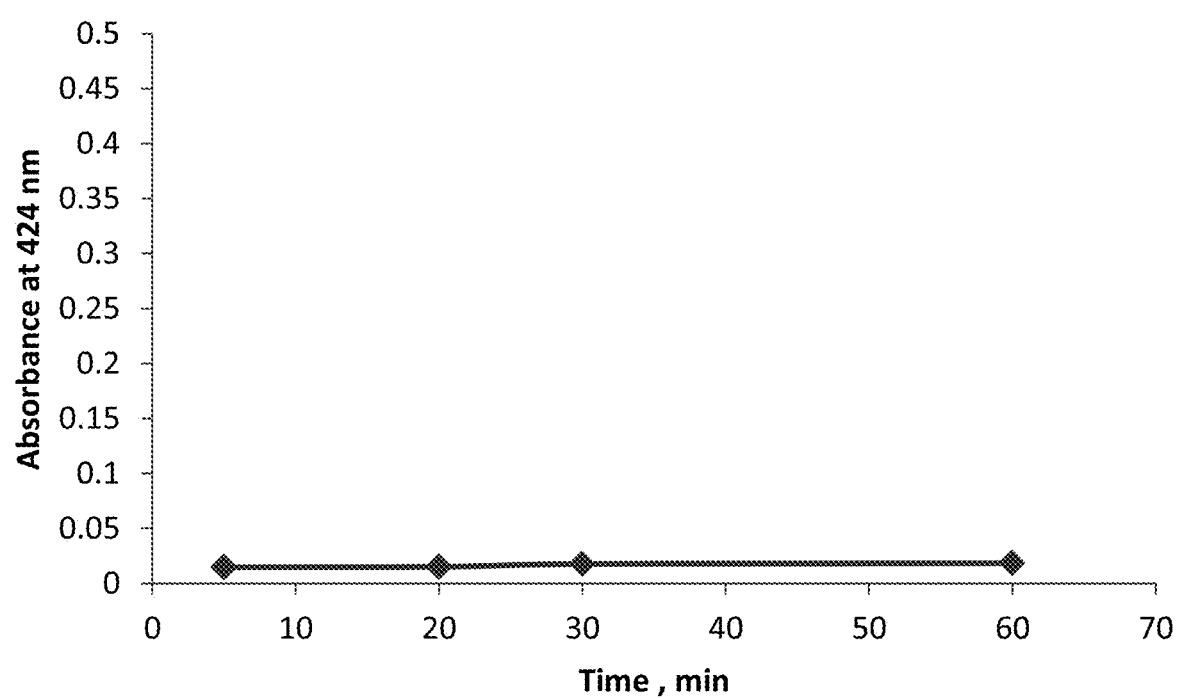
FIG. 3B shows the absorbance measured at 424 nm at different times after mixing of TMB and hydrogen peroxide alone.

The dye used in these experiments, TMB, is capable of detecting both peroxycarboxylic acids and peroxide. The key however is the rate of reaction between the two oxidants and the dye. As can be seen in FIG. 3A and FIG. 3B, the dye specifically reacts with peroxycarboxylic acid and shows a color change without the need for the addition of any other chemical or reactants, while no color change is observed when the dye is mixed with water, acid or hydrogen peroxide. FIG. 3A shows a color change observed upon addition of peroxycarboxylic acid composition with TMB. No color change is observed upon mixing TMB with water, acid, or hydrogen peroxide. Therefore, color formation with the dye is associated with the presence of peroxycarboxylic acid alone and not peroxide. No color change upon mixing TMS and hydrogen peroxide alone is further evidenced by a lack of absorbance at 424 nm, the wavelength corresponding to yellow color, as shown in FIG. 3B. Only when an oxygen catalyst, such as a solution containing molybdate, is added into the mixture of TMB and hydrogen peroxide, the reaction of TMB and hydrogen peroxide results in a yellow color.

Example 2

Correlation Between Concentration of Peracetic Acid and Absorbance at 424 nm

Figure 4:
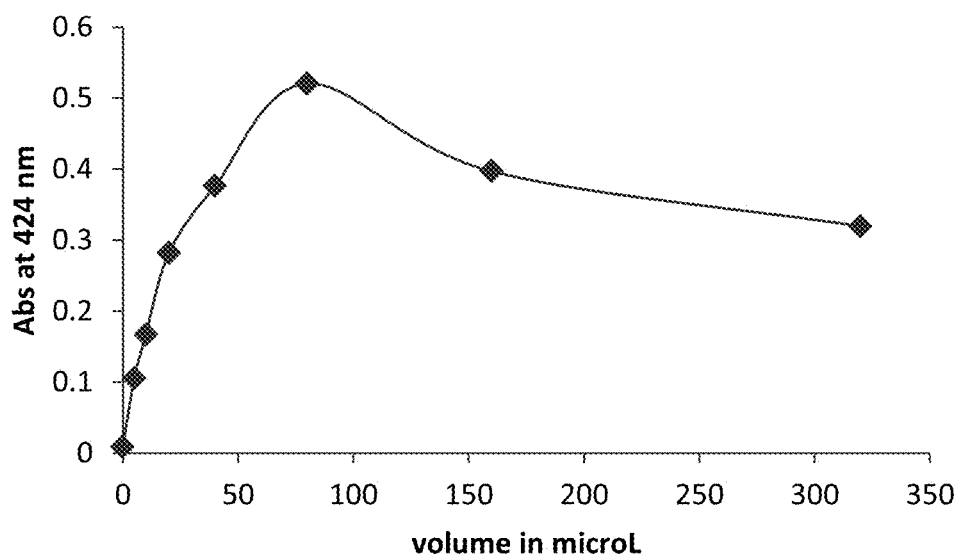
FIG. 4 shows the absorbance value after different volumes (in μL) of a peracetic acid composition were added to a TMB solution.
Figure 5:
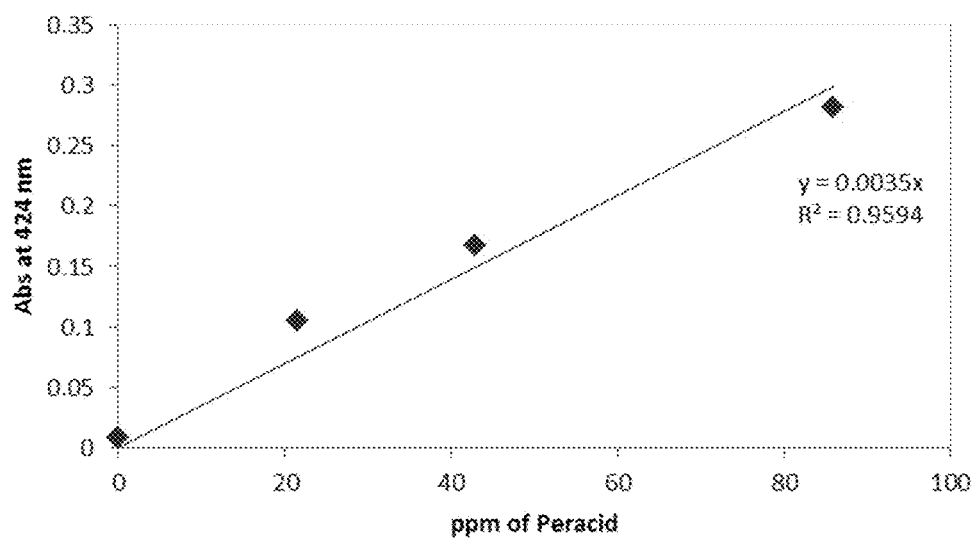
FIG. 5 shows the correlation between the peracetic acid concentration and the absorbance value at 424 nm.

Mixtures of TMB and different amounts (in µL) of peracetic acid composition were created and the absorbance at 424 nm was recorded for each mixture after 15 minutes of mixing. The results are plotted in FIG. 4. As can be seen from FIG. 4, the correlation between absorbance and the concentration of peracetic acid is linear within a range of from about 1 ppm to about 100 ppm. As shown in FIG. 5, beyond about 900 ppm of peracetic acid, the absorbance at 424 nm decreases. This observation sets the limits of peracetic acid concentrations that can be determined with enough precision and necessitates the need to use at least two different dilutions of the tested solution to ensure that the absorbance determinations are performed within the ranges of linearity.

Example 3

Figure 6A:
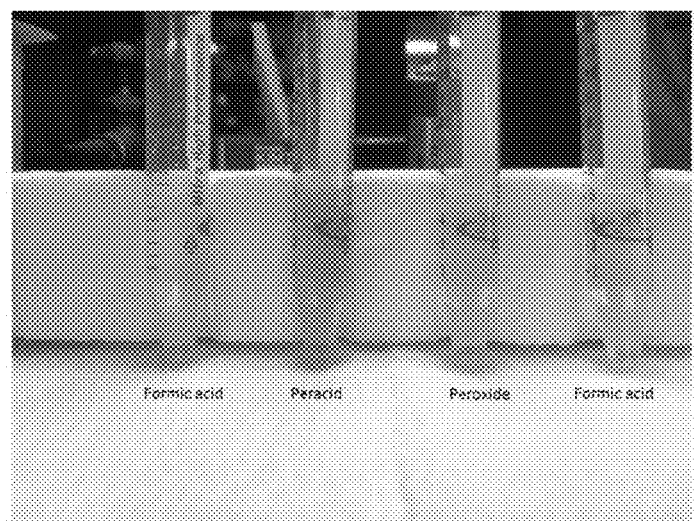
FIG. 6A, FIG. 6B, and FIG. 6C shows the color difference for a TMB solution in the presence of a peroxycarboxylic acid composition, peroxide alone, or acid alone, without presence of molybdate or potassium iodide (FIG. 6A), with presence of molybdate (FIG. 6B), or with presence of potassium iodide (FIG. 6C).
Figure 6B:
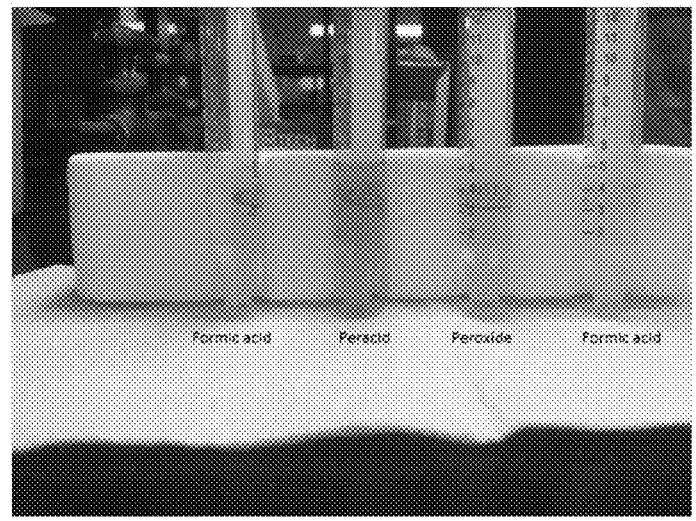
Figure 6C:
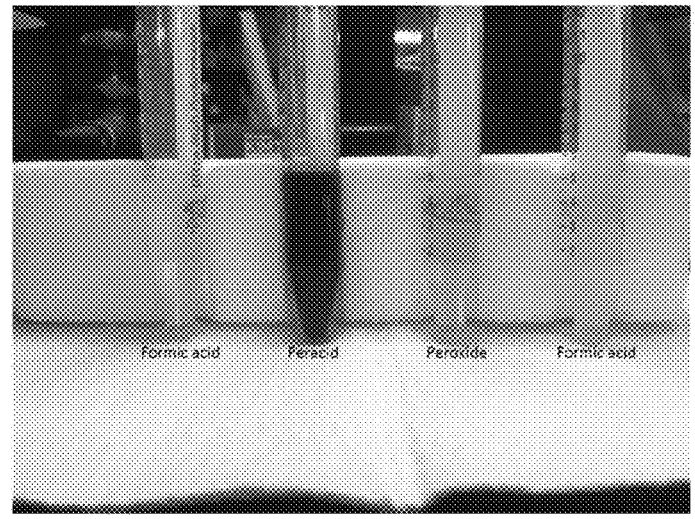

Color Formation of TMB with a Peroxycarboxylic Acid Composition, Hydrogen Peroxide Alone, or Acids Alone with or without the Presence of Molybdate or Potassium Iodine In this Example, color characteristics of TMB solutions with a peracetic acid composition, hydrogen peroxide alone, or acids alone are investigated. The color characteristics of the same TMB solutions but with the presence of a catalyst or potassium iodine were also investigated. The results are shown in FIG. 6A, FIG. 6B, and FIG. 6C. FIG. 6A indicates color formation of TMB in the presence of formic acid alone, peroxycarboxylic acid composition alone, hydrogen peroxide alone, and formic acid alone, respectively. The mixture of TMB and a peroxycarboxylic acid composition shows an intense yellow color while the mixtures of TMB with acids alone or peroxide alone do not show color formation. FIG. 6B shows color formation in the same solutions except with the presence of molybdate as well. With the addition of molybdate, the mixture of TMB and a peroxycarboxylic acid composition shows a similar intense yellow color, while the mixture of TMB and hydrogen peroxide shows mild yellow, and the mixtures of TMB and acids alone are still colorless. FIG. 6C shows color formation in the same solutions with the presence of additional potassium iodide. The mixture of TMB and a peroxycarboxylic acid composition now shows an intense blue color while the other solutions do not show color changes.

What is claimed is:

1. A peroxycarboxylic acid quantification composition comprising:
    a redox sensitive leuco dye, and
    a peroxycarboxylic acid composition comprising an aliphatic $C_1$-$C_{22}$ peroxycarboxylic acid, an aliphatic $C_1$-$C_{22}$ carboxylic acid, and hydrogen peroxide;
    wherein the leuco dye selectively reacts with the peroxycarboxylic acid in the peroxycarboxylic acid composition to form a colored species, and the colored species exhibits a stable absorbance within about 20 minutes at a visible light wavelength and the absorbance intensity is linearly proportional to the concentration of the peroxycarboxylic acid of between about 1 ppm and about 100 ppm.

2. The composition of claim 1, wherein the leuco dye has a concentration of from about 30 ppm to about 1000 ppm in the peroxycarboxylic acid quantification composition.

3. The composition of claim 1, wherein the quantification composition is free of iodide or any other catalysts for the oxidation of the leuco dye.

4. The composition of claim 1, wherein the peroxycarboxylic acid composition is a diluted antimicrobial peroxycarboxylic acid composition, fresh water, pond water, sea water, produced water, or combination thereof,
    wherein the fresh water, pond water, sea water, produced water, or a combination thereof has been treated previously with a peroxycarboxylic acid composition.

5. The composition of claim 1, wherein the peroxycarboxylic acid composition is a water source previously treated with an antimicrobial peroxycarboxylic acid composition.

6. The composition of claim 1, wherein the peroxycarboxylic acid composition is a diluted antimicrobial peroxycarboxylic acid composition.

7. The composition of claim 1, wherein the peroxycarboxylic acid composition comprises peroxyformic acid.

8. The composition of claim 1, wherein the peroxycarboxylic acid composition comprises peroxyacetic acid.

9. The composition of claim 1, wherein the peroxycarboxylic acid composition comprises a combination of aliphatic $C_1$-$C_{22}$ peroxycarboxylic acids.

10. The composition of claim 1, wherein the peroxycarboxylic acid composition comprises one or more sulfonated peracids.

11. The composition of claim 1, wherein the concentration of the $C_1$-$C_{22}$ peroxycarboxylic acid in the peroxycarboxylic acid composition is from about 1 ppm to about 3,000 ppm.

12. The composition of claim 1, wherein the composition has a pH of from about 2 to about 9.

13. The composition of claim 1, wherein the leuco dye is a benzidine or benzidine derivatives.

14. The composition of claim 1, wherein the leuco dye is 3,3',5,5'-tetramethylbenzidine (TMB).

15. The composition of claim 1, wherein the visible light wavelength is from about 400 nm to about 700 nm.

16. The composition of claim 1, wherein the visible light wavelength is about 424 nm.

17. The composition of any one of claims 1-16, wherein the composition is resulted from mixing the leuco dye with the peroxycarboxylic acid composition.

18. A method of quantifying a peroxycarboxylic acid concentration in a treated water source comprising:
    providing a water source,
    contacting the water source with a redox sensitive leuco dye to form the peroxycarboxylic acid quantification composition of claim 1, and
    measuring an absorbance of the peroxycarboxylic acid quantification composition at a visible light wavelength to quantify the peroxycarboxylic acid by using the absorbance-peroxycarboxylic acid concentration standard curve or by comparing the color of the peroxycarboxylic acid quantification composition against a color-peroxycarboxylic acid concentration chart;
    wherein the water source comprises an aliphatic $C_1$-$C_{22}$ peroxycarboxylic acid, an aliphatic $C_1$-$C_{22}$ carboxylic acid, and hydrogen peroxide.

19. A colorimetric assay kit comprising:
    a clear and colorless vial containing a redox sensitive leuco dye; and
    a color-peroxycarboxylic acid concentration chart,
    wherein the vial can receive a certain amount of a peroxycarboxylic acid composition to form the peroxycarboxylic acid quantification composition of claim 1.

* * * * *